United States Patent
Ghosh et al.

(10) Patent No.: US 10,308,603 B2
(45) Date of Patent: Jun. 4, 2019

(54) PROCESS FOR THE SELECTIVE PRODUCTION OF N-METHYL-2-PYRROLIDONE (NMP)

(71) Applicant: COUNCIL OF SCIENTIFIC & INDUSTRIAL RESEARCH, New Delhi (IN)

(72) Inventors: Indrajit Kumar Ghosh, Dehradun (IN); Suman Lata Jain, Dehrandun (IN); Praveen Kumar Khatri, Dehradun (IN); Siddharth Sankar Ray, Dehradun (IN); Madhukar Onkarnath Garg, Dehradun (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 15/749,426

(22) PCT Filed: May 17, 2016

(86) PCT No.: PCT/IN2016/050141
§ 371 (c)(1),
(2) Date: Jan. 31, 2018

(87) PCT Pub. No.: WO2017/021976
PCT Pub. Date: Feb. 9, 2017

(65) Prior Publication Data
US 2018/0222859 A1 Aug. 9, 2018

(30) Foreign Application Priority Data

Jul. 31, 2015 (IN) .......................... 2353/DEL/2015

(51) Int. Cl.
| C07D 207/267 | (2006.01) |
| B01J 29/06 | (2006.01) |
| B01J 29/076 | (2006.01) |
| B01J 29/90 | (2006.01) |
| B01J 35/10 | (2006.01) |

(52) U.S. Cl.
CPC ........ C07D 207/267 (2013.01); B01J 29/061 (2013.01); B01J 29/076 (2013.01); B01J 29/90 (2013.01); B01J 35/1019 (2013.01); *Y02P 20/584* (2015.11)

(58) Field of Classification Search
CPC .................................................. C07D 207/267
See application file for complete search history.

(56) References Cited

U.S. PATENT DOCUMENTS

| 2,964,535 | A | 12/1960 | Clements |
| 6,248,902 | B1 | 6/2001 | Bertola |
| 6,348,601 | B2 | 2/2002 | Ohlbach et al. |
| 6,350,883 | B1 | 2/2002 | Chen et al. |
| 6,987,191 | B1 | 1/2006 | Bertola et al. |
| 7,227,029 | B2 | 6/2007 | Rudloff et al. |
| 2001/0018528 | A1 | 8/2001 | Ohlbach et al. |

FOREIGN PATENT DOCUMENTS

| CN | 1104635 | 7/1995 |
| DE | 2159858 | 6/1973 |
| DE | 4203527 | 8/1993 |
| IN | 4/MUM/2007 | 9/2008 |
| JP | S47-21420 | 6/1972 |
| JP | S49-259 | 1/1974 |
| JP | S49-41364 | 4/1974 |
| JP | S49-020585 | 5/1974 |
| JP | S51-42107 | 11/1976 |
| JP | H10158238 | 6/1998 |
| RO | 113640 | 9/1998 |
| WO | WO 2017/021976 | 2/1917 |
| WO | WO 2009/082086 | 7/2009 |

OTHER PUBLICATIONS

Ullman's Encyclopedia of Industrial Chemistry, 5$^{th}$ Ed., vol. A22, pp. 458-459, 1993.
International Search Report and Written Opinion Issued in Corresponding PCT Application No. PCT/IN2016/050141, dated Sep. 5, 2016.

*Primary Examiner* — Shawquia Jackson
(74) *Attorney, Agent, or Firm* — Norton Rose Fulbright US LLP

(57) ABSTRACT

This invention relates to an improved process for the selective production of N-methyl pyrrolidone (NMP) from gamma-butyrolactone and monomethyl amine preferably in aqueous form in the presence of a catalyst under comparatively milder conditions than the processes well known in the prior art of literature. The process is economically viable as it provides higher yield and selectivity for NMP which reduces the cost of separation of NMP from GBL. The catalyst shows good recyclability without significant loss in catalytic activity and no frequent regeneration is required.

13 Claims, No Drawings

PROCESS FOR THE SELECTIVE PRODUCTION OF N-METHYL-2-PYRROLIDONE (NMP)

CROSS-REFERENCE TO RELATED APPLICATIONS

This application is a national phase application under 35 U.S.C. § 371 of International Application No. PCT/IN2016/050141 filed 17 May 2016, which claims priority to Indian Patent Application No. 2353/DEL/2015 filed 31 Jul. 2015. The entire contents of each of the above-referenced disclosures is specifically incorporated herein by reference without disclaimer.

FIELD OF THE INVENTION

The present invention relates to an improved process for the selective production of N-methyl-2 pyrrolidone (NMP). More particularly, the invention deals with production of 1-methyl 2-pyrrolidone from gamma-butyrolactone and monomethyl amine preferably in aqueous form in presence of a catalyst in a single step at a milder operating condition than the processes known in prior literature. The catalyst is recyclable without loss of activity for a number of runs and does not need regeneration frequently. NMP is used as a solvent in electrochemical and petrochemical industries.

BACKGROUND OF THE INVENTION AND DESCRIPTION OF PRIOR ART

N-methyl-2-pyrrolidone or 1-methyl-2-pyrrolidone (NMP) is a versatile and highly useful chemical which finds large and diverse applications in a wide variety of end uses from electrochemical to petrochemical industries. NMP exhibits higher thermal stability; nontoxicity and having low viscosity which makes it highly useful to be used in chemical synthesis and for the preparation of semiconductors. It is colorless in nature or may be of yellow color depending on the level of impurity present in it. NMP belongs to a class of dipolar aprotic solvents like dimethyl formamide and dimethyl sulphoxide. Due to non-volatile nature and ability to dissolve diverse chemicals, NMP is used as solvent for extracting and recovering certain high value hydrocarbons during petrochemical processing e.g., in the recovery of 1,3-butadiene from cracked $C_4$ stream, and aromatics (BTX) from naphtha/pyrolysis gasoline etc. The NMP extracted 1,3-butadiene from cracked $C_4$ stream from stream crackers is so far the main source of 1,3-butadiene for polymer industries. The good solvency property of NMP also makes it very useful in the polymer industries as a solvent for surface treatment of textiles, resins, and metal coated plastics or as a paint stripper. It is utilized as a solvent in the commercial preparation of polyphenylene sulfide. In the pharmaceutical industry, N-methyl-2-pyrrolidone is used in the formulation for drugs by both oral and transdermal delivery routes.

It is pertinent to mention that the industrial preparation of NMP is predominantly carried out by reaction of gamma-butyrolactone (GBL) with mono methylamine (MMA) in a tubular reactor, e.g. a shaft reactor, at temperature from 200 to 350° C. and super atmospheric pressure, e.g. about 10 MPa (Ullmann's Encyclopedia of Industrial Chemistry, 5th edition, Vol. A22, pages 458 to 459 (1993).

There are several other processes for the synthesis of NMP from gamma-butyrolactone with mono methylamine (MMA) as a starting material.

Reference may be made to several patents (JP7221420, JP7400259, JP7420585, JP7642107) Mitsubishi Chemical Industries Co. Ltd. of Japan described continuous processes for the synthesis of NMP using GBL and MMA as starting materials. The production of NMP was carried out by reactions with high molar ratios between water and shot GBL (typically ranging between 3 and 4 moles of water for each mole of GBL) and by the presence of great amounts of MMA (typically with molar ratios ranging between 1.4-3 moles of MMA per mole of GBL).

Reference may be made to an Indian patent application number: 4/MUM/2007 (publication no. 39/2008) assigned to Balaji Amines Limited discloses a process for the production of NMP from gamma-butyrolactone (GBL) and mono methyl amine (MMA) at a desired molar ratio in a series of reactors operated at temperatures in the range of 200 to 300° C. and pressures in the range of 30 to 90 atmospheric for a residence time of 15 to 150 minutes. NMP thus obtained reported to purity of not less than 99.7% and yield of greater than 90%.

Reference may be made to the U.S. Pat. No. 6,348,601 B2 assigned to BASF discloses a method for N-Methyl-2-pyrrolidone (NMP) production by preparing a mixture comprising monomethylamine, dimethylamine and trimethylamine in a first step by reacting ammonia with methanol at elevated temperature in the range of 300 to 500° C. and pressure in the range of 1500 to 3000 kPa in the presence of a solid acid catalyst and hydrogen, followed by separating off the ammonia and then reacting the mixture comprising methylamines with gamma-butyrolactone (GBL) in a molar ratio of monomethylamine to GBL in the range of 1.05 to 1.5 at temperature 230 to 270° C. and pressure 50 to 150 bar in a second step for a residence time of 2 to 4 hrs. The process elaborated yields NMP at a selectivity of 95% or more at the conversion of GBL of 99%.

Reference may be made to the U.S. Pat. No. 6,248,902B1 assigned to Pantochim S.A., describes a process for the production of N-methyl-pyrrolidone obtained by reaction of gamma-butyrolactone and monomethylamine, wherein the synthesis is carried out by a continuous non-catalytic process in liquid phase, via three distinct reaction stages connected in series. Three reactors operated in the range of temperature 150 to 310° C. and pressure 30 to 90 atmospheric and residence time of 5 to 180 minutes which gives a conversion of GBL of more than 98% with selectivity to NMP 95% or more.

Reference may be made to the U.S. Pat. No. 6,987,191B1 assigned to BASF also discloses a process for the production of N-methyl pyrrolidone using gamma-butyrolactone and mixed methylamines as starting materials, in a continuous process, in such operating conditions as to allow the production of high purity N-methyl-2-pyrrolidone in high yields. The process also consists of three stages in series at operating temperature in the range of 150 to 310° C. and pressure 40 to 100 atmospheric for residence time 15 to 180 minutes. The conversion and selectivity of GBL and NMP reported to be of more than 98% and 95% respectively.

Reference may be made to the Chem. abstracts 124: 145893 (CN-A-11046 35) describes the synthesis of NMP by reaction of GBL with MMA at 220 to 290° C. and 26 MPa (260 bar). The batch wise reaction of a mixture of GBL, 30% strength aqueous MMA and water in a weight ratio of 1:1.4:5.6 at 280° C. and 6 MPa (60 bar) gives NMP in a yield of 97%. The above weight ratio corresponds to a molar ratio of GBL:MMA:$H_2O$ of 1:1.2:26.7 (without taking the water in the MMA solution into account) or a molar ratio of 1:1.2:31.5 (when the water in the MMA solution is taken into account).

Reference may be made to the Chem. abstracts 129:67694 (JP-A2-10158238) relates to the reaction of GBL with from 1.03 to 1.50 molar equivalents of MMA in the presence of from 1.0 to 2.9 molar equivalents of water at from 250 to 300° C. The batch wise reaction of GBL with MMA and water in a molar ratio of 1:1.1:1 at 280° C. for 1 hour gives NMP in a yield of 99.9%.

Reference may be made to the Derwent abstract 1998-607722, Chem. Abstracts 134:178463 (RO-B1-113640) relate to a process for the continuous preparation of NMP in the liquid phase in a two stage procedure. The reaction conditions in the first stage are: molar ratio of GBL, MMA and water: 1:1.2:2.1, temperature of 150 to 170° C. and pressure of 90 to 100 bar. The reaction conditions in the second stage are: 280 to 290° C. and 90 to 100 bar.

Reference may be made to the Chem. abstract 82:139947 (JP-B4-49 020 585) describes the reaction of one part of GBL With two parts of monomethylamine and from 2 to 4 parts of water (molar ratio of 1:5.5:9.6-19.1) at 250° C. for 2 hours to give NMP in a yield of 99%. The temperature range for the reaction is generally from 200 to 300° C., in particular from 230 to 300° C.

Reference may be made to the Chem. abstract 87:5802 (JP-A2-49 041364) discloses the reaction of GBL with monomethylamine and water as a 1:1.4:4 mixture (molar ratio of 1:3.9:19.1) at 250° C. and from 44 to 49 bar.

Reference may be made to the U.S. Pat. No. 7,227,029B2 assigned to BASF describes a process for the continuous preparation of N-methyl-2-pyrrolidone (NMP) by reacting gamma-butyrolactone (GBL) with monomethylamine (MMA) in the liquid Phase, wherein GBL and MMA are used in a molar ratio of from 1:1.08 to 1:2 and the reaction is carried out at from 320 to 380° C. and an absolute pressure of from 70 to 120 bar at a space velocity of 1.4 kg/h of GBL per unit volume of reactor. The process yields NMP at a selectivity of more than 98% under conversion of GBL of more than 98%. The process claims use of an upright tube reactor in which the monomethylamine and the GBL are fed separately at the bottom of the reactor via a two fluid injector provided the feed mixture contains less than 10% by Weight of Water.

Reference may be made to the U.S. Pat. No. 2,964,535 assigned to Monsanto relates to a process for purifying NMP by treatment with an alkali metal hydroxide in aqueous solution and subsequent distillation.

The thermal processes at liquid phase although lead to high NMP yield but they suffer from the following disadvantages:
a. High pressure requirement to carry out the reaction in the liquid phase involves high engineering outlay associated with high capital and operating costs
b. High corrosion rate of aqueous methyl amine solution at high temperature and high pressure reduce the life of equipments and thus increase the capex and opex of the plant
c. Plurality of reaction stages to get the high space time yield of NMP is associated with high capital and operating costs The processes described by Mitsubishi is also disadvantageous in terms of the high costs involved with the separation of excess MMA and its recovery and with the separation of the water forwarded to the reaction to which synthesis water adds up (one mole of water for each mole of reacted GBL).

To avoid the drawbacks associated with the continuous reaction in the presence of excess MMA and water, alternative methodologies have been proposed and these are based on the employment of catalysts.

Reference may be made to the German Patent No. 2,159,858 owned by Mobil Oil a synthesis with GBL and MMA in the presence of 13X type Zeolites is described.

Reference may be made to the German Patent No. 4,203,527 owned by AKZO, a synthesis involving GBL, MMA and steam in the gas phase and at a temperature of 275° C. on a NaX type Zeolite is described.

The above mentioned processes did not succeed in being applied industrially, as the employment of the mentioned catalyst subject to regenerations is disadvantageous in terms of the economic balance of the process as compared with non-catalytic processes.

Thus, the overall drawbacks of the prior art processes to produce NMP are:
a. High pressure requirement to carry out the reaction in the liquid phase involves high engineering outlay associated with high capital and operating costs
b. High corrosion rate of aqueous methyl amine solution at high temperature and high pressure reduce the life of equipments and thus increase the capex and opex of the plant
c. Plurality of reaction stages to get the high space time yield of NMP is associated with high capital and operating costs
d. the high costs involved with the separation of excess MMA and its recovery and with the separation of the MMA.

The need of the present invention from industrial outlook is therefore of utmost importance to produce NMP from GBL and MMA preferably in aqueous form in a typical molar ratio GBL to MMA at a milder condition than that as per the prior art of literatures, in presence of a catalyst which does not need to regenerate frequently. Another potential aspect of the present invention is the low cost of separation of the product as NMP is produced at a very high selectivity ≥99% at the conversion of GBL ≥99%.

Objectives of the Invention

An objective of the present invention is to eliminate the disadvantages of the prior art processes and to provide a one-step catalytic process for producing NMP in high yield Another objective of the present invention is to provide an improved process for the selective production of N-methyl-2-pyrrolidone (NMP) using gamma-butyrolactone, and mono methylamine preferably in aqueous form of concentration of the amine in aqueous solution ranging up to 40% by weight as feed material in a single step.

Yet another objective of this invention is to provide an improved process for the production of NMP in a batch wise operation at a milder operating condition than that stated in the prior literature art; at temperature 130 to 250° C. preferably 150 to 200° C. and pressure 5 to 70 bar preferably 20 to 30 bar and at a period of residence time of 30 to 180 minutes preferably 60 to 120 minutes in presence of a catalyst consisting of an acidic support preferably a bronsted acidic support and modified by at least one of the oxides or in their combination among the metals like Al, Zr, W etc. to the percentage of weight of metal loading of 1 to 30 preferably 5 to 20 more particularly 10 to 15.

Still, another objective of this invention is to propose an improved process for the production of NMP at a selectivity of ≥99% at conversion of GBL ≥99% using MMA in aqueous form and GBL at a molar ratio of GBL to MMA 1:1 to 1:2 preferably 1:1 to 1:1.5 more particularly 1:1 to 1:1.15.

Yet, another objective of this invention is to propose an improved process for the efficient recycling of catalyst without frequent regeneration for the selective production of NMP from GBL and MMA as feedstock.

Still a further objective of this invention is to propose a process for the selective production of NMP from GBL and MMA at a lower cost in comparison to the processes mentioned in the prior art.

SUMMARY OF THE INVENTION

Accordingly, the present invention provides an improved process for the selective production of N-methyl-2-pyrrolidone comprising process steps:

a) reacting feedstock monomethyl amine (MMA) preferably in aqueous form and gamma-butyrolactone (GBL) in a single step in a continuously stirred tank reactor (CSTR) in batch mode at a molar ratio of MMA to GBL in the range of 1 to 2, in the presence of catalyst consisting of a bronsted acidic support which is a class of zeolitic material with $SiO_2$ to $Al_2O_3$ molar ratio of 70 to 100 having specific surface area of 400 to 500 $m^2/g$ and modified by oxide of one or metals selected from Al, Zr, W to the percentage of metal loading of 1 to 30 parts by weight of the support with catalyst content between 1 to 10% of total feedstock, at operating condition of temperature 130 to 250° C. and pressure 5 to 70 at 500 to 1000 agitator speed, for a period of 30 to 180 minutes, b) cooling the reaction mixture to the temperature in the range of 20 to 25° C., c) separating the catalyst from the reaction mixture of step b) by known methods, d) separating the product from reaction mixture of step c) by evaporation or distillation to obtain NMP at selectivity to ≥99% at a conversion of GBL to ≥98%, e) recycling the catalyst to reactor after repeating the steps a) to d) several times.

In an embodiment of the present invention, said MMA is used preferably in aqueous form of concentration by weight of up to 40%.

In another embodiment of the present invention, percentage weight of metal loading in catalyst is preferably 5 to 20, more particularly 10 to 15.

In yet another embodiment of the present invention, the support used in the formulation of the catalyst has preferable $SiO_2$ to $Al_2O_3$ molar ratio of 80 to 90 and preferable specific surface area of 420 to 450 $m^2/g$.

In still another embodiment of the present invention, amount of catalyst used with respect to the total feed is preferably in the range of 1 to 5% by wt.

In still yet another embodiment of the present invention, the catalyst used is in the form of powder to a particle size of 20-30 mesh.

In another embodiment of the present invention, the catalyst used for several runs is recycled back after stirring with a solvent at temperature 60-90° C. under reflux and drying in oven for a period of 6 to 12 hours at 80 to 110° C.

In still another embodiment of the present invention, the solvent used for the washing of the catalyst for recycled use is selected from low boiling chemicals like acetone, dimethylene chloride, benzene, petroleum ether.

In still yet another embodiment of the present invention, purity of NMP is 99.99%.

In yet another embodiment of the present invention, recovered unreacted monomethyl amine is recycled back.

In an embodiment of the present invention, gamma-butyrolactone, and mono methylamine preferably in aqueous form are used as the raw materials for the selective production of NMP.

In yet another embodiment of the present invention, a suitable catalyst used is comprised of an acidic support and modified by metal oxide of one or in combination of the metals like Al, Zr, W at a percentage weight of metal loading by 1 to 30 preferably 5 to 20 more particularly 10 to 15.

In yet another embodiment of the present invention, the catalyst used is prepared by conventional incipient wetness impregnation method by dissolving appropriate quantity of precursor salt of the metal in excess of a low boiling solvent preferably demineralized water and bringing the solution in contact of the support material preferably in powder form and stirring the mixture at temperature in the range of 40 to 60° C. until a slurry is obtained, followed by drying in oven at 110° C. for 6 to 12 hours preferably 8 to 10 hours and finally calcining at 450° C. for a period of 3 to 6 hours preferably 4 to 5 hours under continuous flow of air.

In yet another embodiment of the present invention, the amount of catalyst used with respect to the total feed is in the range of 1 to 10 parts preferably 1 to 5 parts by weight.

In yet another embodiment of the present invention, the catalyst used is in the form of powder to a particle size of 20 to 30 mesh.

In yet another embodiment of the present invention, the catalyst is separated from reaction mixture by filtration and simply recycled for further reactions.

In yet another embodiment of the present invention, the catalyst used for several runs is recycled back after stirring with a solvent at temperature 60 to 90° C. under reflux and drying in oven for a period of 6 to 12 hours at 80 to 110° C.

In yet another embodiment of the present invention, the solvent used for the washing of the catalyst for recycled use may be among the low boiling chemicals like acetone, dimethylene chloride, benzene, petroleum ether etc.

In yet another embodiment of the present invention, pure NMP (99.99%) is obtained by evaporating off the water and methylamine left in the product mixture.

In yet another embodiment of the present invention, recovered unreacted monomethyl amine is recycled back.

DETAILED DESCRIPTION OF THE INVENTION

According to this invention, the process involves the production of N-methyl-2-pyrrolidone (NMP) by reacting monomethyl amine (MMA) preferably in aqueous form with gamma-butyrolactone in a batchwise operation in a single step in a typical CSTR in presence of a catalyst. In an alternative approach, MMA preferably in aqueous form is introduced into the reactor containing GBL and the catalyst premixed under a pressure of 5 to 70 bar preferably 20 to 30 bar. In another alternative approach, GBL is introduced into the reactor containing MMA preferably in aqueous form and the catalyst premixed under a pressure of 5 to 70 bar preferably 20 to 30 bar. The concentration of MMA in aqueous solution may be up to 40% by weight and the MMA is introduced to the reactor at a molar ratio to GBL of 1 to 2 more preferably 1 to 1.5 more particularly 1 to 1.15. The amount of the catalyst used is 1 to 20 parts preferably 1 to 10 parts more particularly 1 to 5 parts by weight of the total feed material. The reaction mixture is then heated to the desired temperature in the range of 130 to 250° C. preferably 150 to 200° C. and kept for residence time of 30 to 180 is minutes preferably 60 to 120 minutes under proper agitation.

The reactor is then cooled down to room temperature and the catalyst is separated by filtration from the reaction product mixture. The reaction product collected is therefore subjected to either of the process of separation by evaporation or distillation to produce NMP at selectivity to ≥99% at a conversion of GBL to ≥98%.

Accordingly, the present invention provides an improved process for the selective production of NMP at a milder condition than the processes mentioned in the prior art of literature in presence of a catalyst.

In accordance with the present invention, the catalyst used is a typical acidic catalyst consisting of a bronsted acidic support and modified by oxide of one or in their combination among Al, Zr, W to the percentage of metal loading of 1 to 30 parts preferably 5 to 20 parts more particularly 10 to 15 parts by weight of the support.

In accordance with the present invention, the catalyst used is prepared by conventional incipient wetness impregnation method by dissolving appropriate quantity of precursor salt of the metal in excess of a low boiling solvent preferably demineralized water and bringing the solution in contact of the support material preferably in powder form and stirring the mixture at temperature in the range of 40 to 60° C. until a slurry is obtained, followed by drying in oven at 110° C. for 6 to 12 hours preferably 8 to 10 hours and finally calcining at 450° C. for a period of 3 to 6 hours preferably 4 to 5 hours under continuous flow of air.

In accordance with this invention, the support used in the formulation of the catalyst is a class of zeolitic material with $SiO_2$ to $Al_2O_3$ mole ratio of 70 to 100 preferably 80 to 90 having specific surface area of 400 to 500 m²/g preferably 420 to 450 m²/g.

In accordance with this invention, the catalyst used is in the form of powder to a particle size of 20 to 30 mesh.

In accordance with this invention, the catalyst can be recycled back without any drastic change in activity after several runs.

In accordance with this invention, the catalyst is thoroughly washed after number of experiments by stirring with a low boiling solvent like acetone, dimethylene chloride, benzene, methanol, petroleum ether etc. at temperature of 60 to 90° C. under reflux followed by drying in oven at 80 to 110° C. for a period of 6 to 12 hrs.

In accordance with this invention the pure NMP is obtained after separation of water and MMA either by evaporation or distillation. The recovered MMA can further be used up in the process mentioned herein.

The invention as described in detail in the examples given below which are provided by way of illustration only and therefore should not be construed to limit the scope of the present invention.

EXAMPLES

The synthesis of NMP was carried out under the conditions indicated below in a batch CSTR consisting of a reactor vessel of volume 100 ml and made of high quality stainless steel. The reactor is fitted with an agitator which enables to mix the reactants with catalyst, a thermocouple inside the vessel that detects the reaction mixture temperature and a probe that detects the pressure inside the vessel. The pressure inside the vessel is maintained by using nitrogen gas supplied from a high pressure cylinder during the filling of reactants into the vessel. The external heating jacket enables to achieve the reaction temperature in the vessel very smoothly. For the safety precautions, the vessel is filled with reactants and catalyst up to 50% volume of the vessel. The agitator can be adjusted to a speed of maximum up to 3000 rpm in order to mix up the reactants with catalyst very well. Once the residence time gets over, the reaction is quenched by cooling the reactor vessel with ice water to bring the content of the vessel at room temperature. The pressure is released from vent valve and the content of the mixture is employed to filtration for the separation of the catalyst. Once the catalyst is separated, the product mixture is employed for evaporation of water and unreacted MMA from the solution. The catalyst so separated is directly used for recycle experiments The products left after evaporation of the lighters, are then analyzed by Gas Chromatography equipped with a FID detector precalibrated to measure the content of GBL, NMP and by-products to finally calculate the conversion of GBL and selectivity to NMP production as per:

$$\text{Conversion}(\%) = \frac{\text{moles of } GBL \text{ in feed-moles of } GBL \text{ in product}}{\text{moles of } GBL \text{ in feed}} \times 100$$

$$\text{selectivity}(\%) = \frac{\text{moles at } NMP \text{ in product}}{\text{moles of } GBL \text{ in feed-moles of } GBL \text{ in product}} \times 100$$

The catalyst used is comprised of 15% of Al in the form of oxide loaded on H-ZSM-5 ($SiO_2$ to $Al_2O_3$ molar ratio 80, typical surface area of 425 m²/g) in the reaction mentioned above. The catalyst is prepared by dissolving 21.2805 g of $Al(NO_3)_3 \cdot 9H_2O$ in about 40 ml of demineralized water and stirred with 10 g of powdered HZSM-5 at temperature 60° C. until a thick slurry is obtained. The slurry is then kept at room temperature for 24 hours and dried in oven at 110° C. for 12 hours. Final catalyst is obtained after calcination of the dried material in a tubular furnace by heating it up to temperature of 450° C. at a ramp of 2° C./min and keeping at 450° C. for 5 hours under a constant flow of air.

Following are the condition and result of the experiments.

| Experiment No. | Temperature (° C.) | Pressure (bar) | Molar ratio: MMA to GBL | Residence time (minute) | Agitator speed (rpm) | GBL conversion (%) | Selectivity for NMP (%) |
|---|---|---|---|---|---|---|---|
| 1 | 150 | 30 | 1 | 120 | 500 | 99.876 | 99.94 |
| 2* | 200 | 25 | 1 | 90 | 500 | 99.85 | 99.92 |
| 3* | 200 | 25 | 1.15 | 120 | 500 | 99.55 | 99.65 |
| 4 | 200 | 30 | 1.15 | 120 | 1000 | 99.5 | 98.95 |
| 5 | 200 | 30 | 1.15 | 120 | 500 | 80.35 | 78.5 |
| 6 | 200 | 30 | 1.15 | 120 | 500 | 94.56 | 93.5 |
| 7 | 200 | 30 | 1.15 | 120 | 500 | 95.78 | 93.55 |
| 8 | 200 | 30 | 1.15 | 120 | 500 | 96.35 | 95.66 |
| 9 | 200 | 30 | 1.15 | 120 | 500 | 99.85 | 99.89 |
| 10 | 200 | 30 | 1.15 | 120 | 500 | 99.95 | 99.65 |

-continued

| Experiment No. | Temperature (° C.) | Pressure (bar) | Molar ratio: MMA to GBL | Residence time (minute) | Agitator speed (rpm) | GBL conversion (%) | Selectivity for NMP (%) |
|---|---|---|---|---|---|---|---|
| 11 | 200 | 30 | 1.15 | 120 | 500 | 93.5 | 92.00 |
| 12 | 200 | 30 | 1.15 | 120 | 500 | 92.25 | 90.75 |

(*with recycled catalyst)

The catalyst combination used for the above experiments:

| Experiment No. | % Al loading in the form of oxide (% weight) | Catalyst content with respect to the total feed content (% weight) |
|---|---|---|
| 1 | 15 | 1 |
| 2* | 15 | 1 |
| 3* | 15 | 1 |
| 4 | 15 | 1 |
| 5 | 0 | 1 |
| 6 | 5 | 1 |
| 7 | 10 | 1 |
| 8 | 20 | 1 |
| 9 | 15 | 3 |
| 10 | 15 | 5 |
| 11 | 5 (% Zr loading in the form of oxide) | 1 |
| 12 | 5 (% W loading in the form of oxide) | 1 |

(*with recycled catalyst)

Advantages of the Present Invention

The present process produces NMP at high selectivity from MMA preferably in aqueous form and GBL at milder condition than that stated in prior art of literature.

The present invention uses a catalyst that can be used for a number of runs at a stretch without necessity of regeneration frequently.

The present invention provides a low cost process for the production of NMP.

The invention claimed is:

1. A process for selective production of N-methyl-2-pyrrolidone (NMP) comprising:
   a) reacting feedstock monomethyl amine (MMA) and gamma-butyrolactone (GBL) in a single step in a continuously stirred tank reactor (CSTR) at a molar ratio of MMA to GBL in the range of 1 to 2, in the presence of catalyst wherein the catalyst comprises 5-15% of Al and consists of a bronsted acidic support which is a class of zeolitic material with $SiO_2$ to $Al_2O_3$ molar ratio of 70 to 100 having specific surface area of 400 to 500 m²/g and modified by oxide of one or more metals selected from Zr and W to the percentage of metal loading of 1 to 30 parts by weight of the support with catalyst content between 1 to 10% of total feedstock, at operating condition of temperature 130 to 250° C. and pressure 5 to 70 at 500 to 1000 agitator speed, for a period of 30 to 180 minutes to obtain a reaction mixture;
   b) cooling the reaction mixture to a temperature in the range of 20 to 25° C.;
   c) separating the catalyst from the reaction mixture of step b) by known methods;
   d) separating the product from reaction mixture of step c) by evaporation or distillation to obtain NMP at selectivity to ≥99% at a conversion of GBL to ≥98%; and
   e) recycling the catalyst to reactor after repeating the steps a) to d) several times.

2. The process of claim 1, wherein said MMA is in aqueous form.

3. The process of claim 2, wherein said MMA is in concentration by weight of up to 40%.

4. The process of claim 1, wherein percentage weight of metal loading in catalyst is 5 to 20.

5. The process of claim 4, wherein percentage weight of metal loading in catalyst is 10 to 15.

6. The process of claim 1, wherein the support used in the formulation of the catalyst has $SiO_2$ to $Al_2O_3$ molar ratio of 80 to 90 and specific surface area of 420 to 450 m²/g.

7. The process of claim 1, wherein amount of catalyst used with respect to the total feed is in a range of 1 to 5% by wt.

8. The process of claim 1, wherein the catalyst used is in the form of powder to a particle size of 20-30 mesh.

9. The process of claim 1, wherein the catalyst used for several runs is recycled back after stirring with a solvent at temperature 60-90° C. under reflux and drying in oven for a period of 6 to 12 hours at 80 to 110° C.

10. The process of claim 9, wherein the solvent used for the washing of the catalyst for recycled use is a low boiling chemical.

11. The process of claim 10, wherein the low boiling chemical is acetone, dimethylene chloride, benzene, or petroleum ether.

12. The process of claim 1, wherein purity of NMP is 99.99%.

13. The process of claim 1, wherein recovered unreacted monomethyl amine is recycled back.

* * * * *